US010550057B1

(12) United States Patent
Boone

(10) Patent No.: US 10,550,057 B1
(45) Date of Patent: Feb. 4, 2020

(54) METHOD OF MAKING A DIALDEYHDE

(71) Applicant: Eastman Chemical Company, Kingsport, TN (US)

(72) Inventor: Matthew Allen Boone, Kingsport, TN (US)

(73) Assignee: Eastman Chemical Company, Kingsport, TN (US)

(*) Notice: Subject to any disclaimer, the term of this patent is extended or adjusted under 35 U.S.C. 154(b) by 0 days.

(21) Appl. No.: 16/559,977

(22) Filed: Sep. 4, 2019

(51) Int. Cl.
C07C 45/58 (2006.01)
C07C 45/51 (2006.01)
C07C 47/133 (2006.01)

(52) U.S. Cl.
CPC .......... C07C 45/511 (2013.01); C07C 47/133 (2013.01)

(58) Field of Classification Search
CPC ............................ C07C 45/511; C07C 45/58
See application file for complete search history.

(56) References Cited

U.S. PATENT DOCUMENTS

| 2,578,724 | A | 12/1951 | Mertzweiller |
| 4,839,413 | A | 6/1989 | Kiehlbauch et al. |
| 4,927,876 | A | 5/1990 | Coogan et al. |
| 4,939,233 | A | 7/1990 | Jenkins et al. |
| 4,946,932 | A | 8/1990 | Jenkins |
| 5,137,961 | A | 8/1992 | Goos et al. |
| 5,247,040 | A | 9/1993 | Amick et al. |
| 5,296,530 | A | 3/1994 | Bors et al. |
| 5,484,849 | A | 1/1996 | Bors et al. |
| 6,451,380 | B1 | 9/2002 | Speece, Jr. et al. |
| 6,743,748 | B2 | 6/2004 | Mizuno et al. |
| 7,208,545 | B1 | 4/2007 | Brunner et al. |
| 9,932,486 | B1 | 4/2018 | Cogar et al. |
| 2009/0076311 | A1* | 3/2009 | Sato ........................ C07C 45/58 568/483 |
| 2012/0289721 | A1* | 11/2012 | End .......................... C07C 45/30 549/519 |
| 2015/0239816 | A1* | 8/2015 | Zaragoza Doerwald ..................... C07D 233/56 568/426 |

FOREIGN PATENT DOCUMENTS

EP 0 492 847 A2 7/1992
WO WO 2007/094922 A2 8/2007

OTHER PUBLICATIONS

Robinson et al. Epoxide ring-opening and Meinwald rearrangement reactions of epoxides catalyzed by mesoporous aliminosilicates. Org. Biolmol. Chem., vol. 7, 2559-2564. (Year: 2009).*
Co-pending U.S. Appl. No. 16/559,842, filed Sep. 4, 2019; Boone.
Co-pending U.S. Appl. No. 16/559,871, filed Sep. 4, 2019; Boone.
Co-pending U.S. Appl. No. 16/559,887, filed Sep. 4, 2019; Boone.
Co-pending U.S. Appl. No. 16/559,912, filed Sep. 4, 2019; Boone.
Co-pending U.S. Appl. No. 16/559,897, filed Sep. 4, 2019; Boone.
Co-pending U.S. Appl. No. 16/559,880, filed Sep. 4, 2019; Boone et al.
Co-pending U.S. Appl. No. 16/559,859, filed Sep. 4, 2019; Boone et al.
Co-pending U.S. Appl. No. 16/560,146, filed Sep. 4, 2019; Boone et al.
Co-pending U.S. Appl. No. 16/560,161, filed Sep. 4, 2019; Boone et al.
Co-pending U.S. Appl. No. 16/559,988, filed Sep. 4, 2019; Boone et al.
ASTM D1544; Standard Test Method for Color of Transparent Liquids (Gardner Color Scale).
ASTM D2354-10$^{e1}$; Standard Test Method for Minimum Film Formation Temperature (MFFT) of Emulsion Vehicles.
ASTM D4946; Standard Test Method for Blocking Resistance of Architectural Paints.
ASTM D6886; Standard Test Method for Determination of the Weight Percent Individual Volatile Organic Compounds in Waterborne Air-Dry Coatings by Gas Chromatography.
Burczyk, B. et al.; "Relations between chemical structure and surface activity I: Synthesis and properties of aqueous solutions of acetals formed from aliphatic aldehydes and monoalkyl ethers of ethylene glycols;" Tenside Detergents; 15(2); 1978; pp. 68-71.
Burczyk, B. et al.; "Surface Properties of Selected Linear and Cyclic Acetals;" Tensioactivos: Biodegradabilidad, Fis.-Quim. Apl., Jorn. Com. Esp. Deterg.; 11$^{th}$; 1980; pp. 581-601.
Cohen, R. et al.; "Foam stabilizing properties of linear acetals containing oxyethylene units in their molecules;" Tenside Detergents; 18 (4); 1981; pp. 202-205.
Duchene, A. et al.; "Alxoxyméthyltributylétains précurseurs d'alcoxyméthyllithiums : application à la synthèse de monoéthers d'α-glycols et à l'homologation de cétones en aldéhydes;" Bulletin De La Societe Chimique De France; 1985; No. 5; pp. 787-792.
Getzkin, AJ. et al.; "Synthesis of Some Symmetrical Aldehyde Glycol Monoether Acetals;" Journal of the American Pharmaceutical Association, Scientific Edition; 49; 1960; pp. 746-750.
Kanno, T. et al.; "Oxygenation of Aromatic Vinyl Ethers. A Noticeable Formation of Epoxides and Reaction Mechanism;" Bull. Chem. Soc. Jpn.; 54; 1981; pp. 2330-2336.
Moszner, N. et al.; "Reaction behavior of monomeric β-ketoesters. 2. Synthesis, characterization and polymerization of methacrylate group containing enamines;" Polymer Bulletin; 32; pp. 419-426; (1994).
Presidential Green Chemistry Challenge: 2005 Designing Greener Chemical Award; Archer Daniels Midland Company; Archer RC™: A Nonvolatile, Reactive Coalescent for the Reduction of VOCs in Latex Paints; United States Environmental Protection Agency; Accessed via the web on Jun. 6, 2018; https://www.epa.gov/greenchemistry/presidential-green-chemistry-challenge-2005-designing-greener-chemicals-award.

(Continued)

Primary Examiner — Sikarl A Witherspoon
(74) Attorney, Agent, or Firm — Matthew W. Smith

(57) ABSTRACT

Disclosed is a two-step process to make a dialdehyde. In the process a diepoxide is first hydrolyzed with an alcohol solvent to an intermediate which is then subjected to a double-Pinacol rearrangement to obtain a dialdehyde. The dialdehydes have utility as chemical intermediates, and particular utility in processes to make enol ether compounds which can be used in applications as plasticizers, diluents, wetting agents, coalescing aids and as intermediates in chemical processes.

4 Claims, No Drawings

(56) References Cited

OTHER PUBLICATIONS

Safa, K. et al.; "1,4-bis[2,2-bis(trimethylsilyl)ethenyl]benzene: Regioselective ring opening of its a,B-eposybix(silane) with some nucleophiles;" Journal of Organometallic Chemistry; 694; 20019; pp. 1907-1911.

Smith, O.W. et al.; "New vinyl ester monomers for emulsion polymers;" Progress in Organic Coatings; 22; 1993; pp. 19-25.

Sokolowski, A. et al.; "Acetals and Ethers. Part IV. Synthesis of Acetals from Aliphatic Aldehydes and Monoalkyl Ether of Ethylene Glycols;" Polish Journal of Chemistry (formerly Roczniki Chemii); 53(4); 1979; pp. 905-912.

Sokolowski, A. et al.; "Statistical Evaluation of the Influence of Linear Acetal Structures on Their Adsorption at the Aqueous Solution-Air Interface;" Comunicaciones presentadas a las XII Jornadas del Comite Espanol de la Detergencia; Asociacion De Investigacion De Detergentes, Tens; 1981; pp. 491-507.

* cited by examiner

METHOD OF MAKING A DIALDEYHDE

FIELD OF THE INVENTION

This application relates to chemistry generally. In particular, this application relates to a novel method of making dialdehydes from diepoxides.

BACKGROUND OF THE INVENTION

Mono-epoxide to mono-aldehyde rearrangements are well known in the chemical arts. However, di-epoxide rearrangement to di-aldehyde processes are less known. For example, common Lewis acids and Bronsted acids lead to oligomerization and the production of complex mixtures of products when a difunctional rearrangement is attempted.

Di-aldehydes are particularly useful as chemical intermediates to make material such as enol ethers. It would be desirable to have an efficient process to make dialdehydes from diepoxides. The invention disclosed herein describes a two-step process to make a dialdehyde wherein a diepoxide is first hydrolyzed with an alcohol solvent to an intermediate which is then subjected to a double-Pinacol rearrangement to obtain a dialdehyde.

SUMMARY OF THE INVENTION

The Invention is set forth in the appended claims.

In an embodiment this invention comprises a method for making dialdehydes from diepoxides comprising:
a) combining an alcohol with a diepoxide in the presence of a base to form a first mixture;
b) heating said first mixture to form a second mixture;
c) adding an acid to the second mixture to form a third mixture; and
d) separating dialdehyde from the third mixture.

DETAILED DESCRIPTION

Definitions

In this specification and in the claims that follow, reference will be made to a number of terms, which shall be defined to have the following meanings.

"Alcohol" means a chemical containing one or more hydroxyl groups.

"Aldehyde" means a chemical containing one or more —C(O)H groups.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

Presented herein is a process to directly convert a diepoxide to a dialdehyde via a novel synthesis method.

Mono-epoxide to mono-aldehyde rearrangements are well known. However, when attempting to extend scope to di-aldehyde to di-epoxide rearrangement, there are few chemistry options. For example, common Lewis acids and Bronsted acids lead to oligomerization and the production of complex mixtures of products when a difunctional rearrangement is attempted. The inventors tested tritylium tetrafluorborate, boron trifluoride, zinc chloride, methanesulfonic acid, solid supported acids (e.g. Amberlyst™ 15, Nafion™ NR50)—all of which led to oligomerization. Other catalysts that have were screened include kaolinte, bentonite, Zeolite Y, acidic aluminum oxide, and silica gel. These processes all resulted in no reaction.

We have discovered a two-step process employing methanolysis of an aromatic diepoxide to a dicarbinol followed by an acid-catalyzed rearrangement to successfully produced dialdehydes.

The method comprises:
a) combining an alcohol with a diepoxide in the presence of a base to form a first mixture;
b) heating said first mixture to form a second mixture;
c) adding an acid to the second mixture to form a third mixture; and
d) separating dialdehyde from the third mixture.

Di-epoxides suitable for the method include 1,3-bis(2-methyloxiran-2-yl)benzene, 1,4-bis(2-methyloxiran-2-yl)benzene, 1,3-di(oxiran-2-yl)benzene, 1,4-di(oxiran-2-yl)benzene 4,4'-bis(2-methyloxiran-2-yl)-1,1'-biphenyl, and 2,6-bis(2-methyloxiran-2-yl)naphthalene and mixtures thereof.

Acids suitable for the method include acetic acid, formic acid, chloroacetic acid, dichloroacetic acid, trichloroacetic acid, and trifluoroacetic acid and mixtures thereof.

Alcohols suitable for the method include methanol, ethanol, n- and iso-propanol, n-butanol, and sec-butanol and mixtures thereof.

This invention can be further illustrated by the following examples thereof, although it will be understood that these examples are included merely for purposes of illustration and are not intended to limit the scope of the invention unless otherwise specifically indicated.

Abbreviations wt % is weight percent; hrs or h is hour(s); mm is millimeter; m is meter; GC is gas chromatography; ° C. is degree Celsius; min is minute; $t_R$ is retention time; g is gram; mmol is millimole; mol is mole; mL is milliliter; L is liter; μL is microliter.

EXAMPLES

Example 1: Preparation of 2,2'(1,4-phenylene)bis(1-methoxypropan-2-ol) [2]

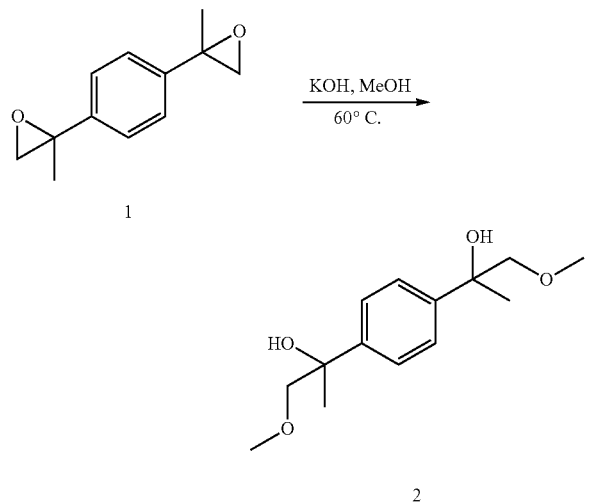

KOH (49.2 g, 788 mmol) was dissolved in MeOH (400 mL) contained within a 1 L, 4-necked round-bottom flask fitted with thermocouple, overhead stirrer, and nitrogen inlet atop a reflux condenser. During the addition of KOH, internal temperature reached 60° C. and was maintained there by heating mantle. 1,4-bis(2-methyloxiran-2-yl)benzene [1] was added over the course of 1.5 hrs. The reaction was monitored by $^1$H NMR (aliquot was taken and dissolved in DMSO-$d_6$. Once the di-epoxide was completely consumed, the reaction was cooled to ambient temperature, and acetic acid (47.3 g, 788 mmol) was added dropwise. Once addition was complete, the volatiles were removed under reduced pressure using a rotary evaporator. The residue was taken up in 250 mL of toluene and then washed with 250 mL of water. The aqueous layer was back-extracted with 250 mL of EtOAc using a separatory funnel. The organics were combined, dried with MgSO$_4$ and simultaneously treated with 5 g of activated carbon. The mixture was filtered, and volatiles were removed under reduced pressure using a rotary evaporator. 2,2'-(1,4-phenylene)bis(1-methoxypropan-2-ol) [2] was isolated as a white solid [LC-MS (Column A) $t_R$: 3.80 min (Exact mass: 254.15 m/z, found 254.2 m/z)]/.

Example 2: Preparation of 2,2'-(1,4-phenylene)dipropanal [3]

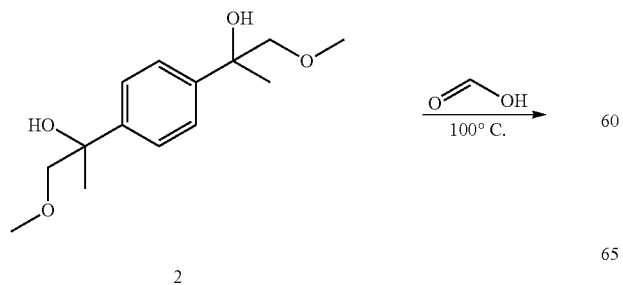

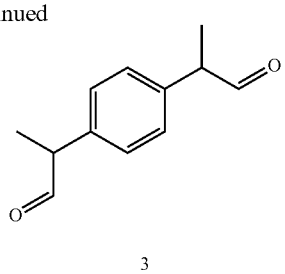

The 2,2'-(1,4-phenylene)bis(1-methoxypropan-2-ol) [2] then dissolved in formic acid (88%, 98.0 g) contained within a 500 mL, 4-necked round-bottom flask fitted with thermocouple, overhead stirrer, and nitrogen inlet atop a reflux condenser. The mixture was heated to 100° C. After 6 hrs, additional formic acid was added (98.0 g). After an additional 2 hrs, GC indicated >99% conversion to 2,2'-(1,4-phenylene)dipropanal [3]. The volatiles were then removed under reduced pressure using a rotary evaporator. The residue was taken up in 250 mL of toluene and then washed with a saturated solution of NaHCO$_3$. After layer separation, the organics were dried with MgSO$_4$, filtered, and then concentrated. The crude material was then Kugelrohr—distilled at 150° C./1 mm Hg to isolate the 2,2'-(1,4-phenylene)dipropanal [3] as a colorless oil. GC-MS $t_R$: 14.47 min (Exact mass: 190.10 m/z, found: 190.1 m/z).

Example 3: Preparation of 2,2'-(1,3-phenylene)bis(1-methoxypropan-2-ol) 5 and 2,2'-(1,3-phenylene)dipropanal [6]

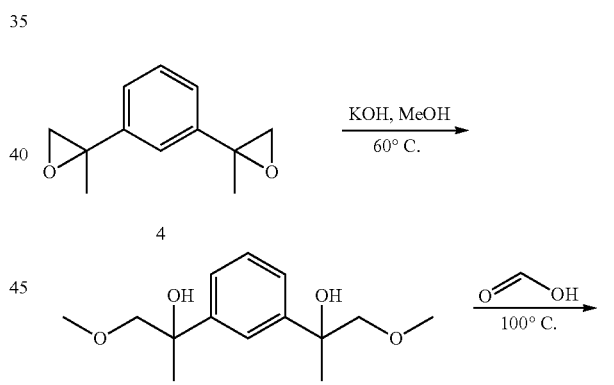

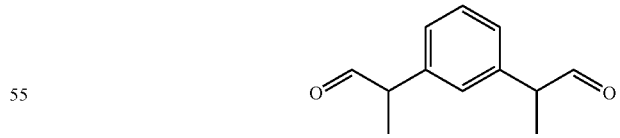

2,2'-(1,3-phenylene)bis(1-methoxypropan-2-ol) [5] was prepared in a similar manner to 2,2'-(1,4-phenylene)bis(1-methoxypropan-2-ol) [2] using the dicarbinol preparation procedure described herein above. [LC-MS (Column B) $t_R$: 4.55 min, 4.68 min (Exact mass: 254.15 m/z, found 254.2 m/z)]. 2,2'-(1,3-phenylene)dipropanal [6] was prepared using the di-aldehyde preparation procedure described herein above. [GC-MS $t_R$: 14.22 min (Exact mass: 190.10 m/z, found: 190.1 m/z)].

Instrument Parameters—Agilent 6890N GC with Agilent 5975B VL MSD

Sample Prep: 100 μL sample diluted to 1 mL with toluene; Column: DB-5 30 m×0.25 mm×0.25 μm; Oven Ramp: 0-4.5 mins at 40° C.; Ramp 20 C/min to 280 C, Hold up to 85 mins; Injector: Temperature—250° C.; Split Flow—65 mL/min; Carrier Flow Rate—1.3 mL/min; Volume—1.0 μL; MS: Transfer Line—280° C.; Ion Source Temp—230° C.; Mass Range—34-700 amu.

Conditions—Agilent 1100 LC
Sample Prep: 2-3 mg/mL in DMSO
Column A: Zorbax™ XDB-C18×4.6 mm, 5 μm
Column B: Poroshell™ EC-C18 50×4.6 mm, 2.7 μm
Column Temp: 40° C.
Injection Volume: 2 μL
DAD: 190-600 nm collection
Pump Conditions: Initial—97% water (2.5 mM NH$_4$OAc) (Solvent A) and 3% acetonitrile (Solvent B)
Gradient:

| Time (min) | % Solvent A | % Solvent B | Flow (mL/min) |
|---|---|---|---|
| 0 | 97 | 3 | 1.0 |
| 10 | 0 | 100 | 1.0 |
| 25 | 0 | 100 | 1.0 |
| 25.1 | 97 | 3 | 1.0 |
| 30 | 97 | 3 | 1.0 |

Mass spectra were acquired with a Micromass LCT mass spectrometer, which was coupled to the LC. Mass spectra were collected using electrospray ionization in both the positive-ion and negative ion modes. Ammonium acetate (50 mM in MeOH) was added post column (0.1 mL/min) to enhance ionization efficiency. ES$_+$/ES$_-$ scan range was 60-3300 amu (25 and 75V).

The invention has been described in detail with reference to the embodiments disclosed herein, but it will be understood that variations and modifications can be effected within the spirit and scope of the invention.

I claim:

1. A method for making dialdehydes from diepoxides comprising:
    a) combining an alcohol with a diepoxide in the presence of a base to form a first mixture;
    b) heating said first mixture to form a second mixture;
    c) adding an acid to the second mixture to form a third mixture; and
    d) separating dialdehyde from the third mixture.

2. The method of claim 1 wherein said diepoxide is selected from the group comprising 1,3-bis(2-methyloxiran-2-yl)benzene, 1,4-bis(2-methyloxiran-2-yl)benzene, 1,3-di(oxiran-2-yl)benzene, 1,4-di(oxiran-2-yl)benzene 4,4'-bis(2-methyloxiran-2-yl)-1,1'-biphenyl, and 2,6-bis(2-methyloxiran-2-yl)naphthalene and mixtures thereof.

3. The method of claim 1 wherein said alcohol is selected from the group consisting of methanol, ethanol, n- and iso-propanol, n-butanol, and sec-butanol and mixtures thereof.

4. The method of claim 1 wherein said acid is selected from the group consisting of acetic acid, formic acid, chloroacetic acid, dichloroacetic acid, trichloroacetic acid, and trifluoroacetic acid and mixtures thereof.

* * * * *